United States Patent [19]

Hadden et al.

[11] 4,260,950

[45] Apr. 7, 1981

[54] AUTOMATIC PORTABLE PH METER AND METHOD WITH CALIBRATION RECEPTACLE

[75] Inventors: David M. Hadden, Los Altos; Eric S. Micko, Los Altos Hills, both of Calif.

[73] Assignee: Delphian Corporation, Sunnyvale, Calif.

[21] Appl. No.: 54,688

[22] Filed: Jul. 5, 1979

[51] Int. Cl.³ ............................................. G01N 27/42
[52] U.S. Cl. .................................... 324/438; 324/425; 73/1 R
[58] Field of Search ...................... 73/1 R, 1 F, 1 G; 324/438, 425; 204/195 R, 195 H, 195 G, 1 H

[56] References Cited

U.S. PATENT DOCUMENTS

| | | | |
|---|---|---|---|
| 3,889,255 | 6/1975 | Pettersen | 73/1 R |
| 4,124,475 | 11/1978 | Zetter et al. | 324/425 |

Primary Examiner—David K. Moore
Attorney, Agent, or Firm—Fitch, Even, Tabin, Flannery & Welsh

[57] ABSTRACT

A portable self-calibrating pH meter particularly adapted for use by unskilled operators in adverse environment conditions is disclosed which has a minimum of operator controls while preventing operator errors and while providing effective and accurate pH measurement.

8 Claims, 7 Drawing Figures

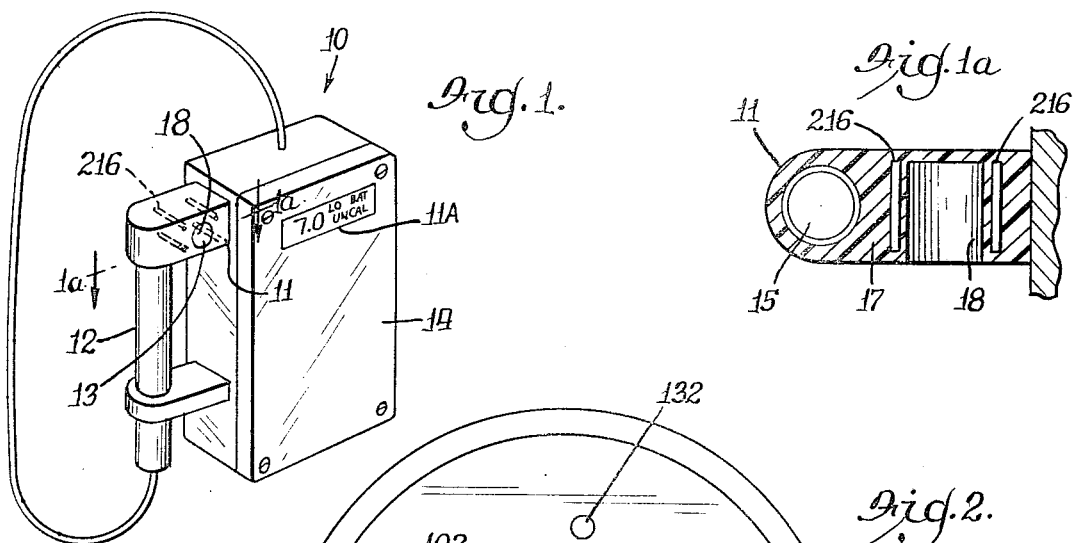
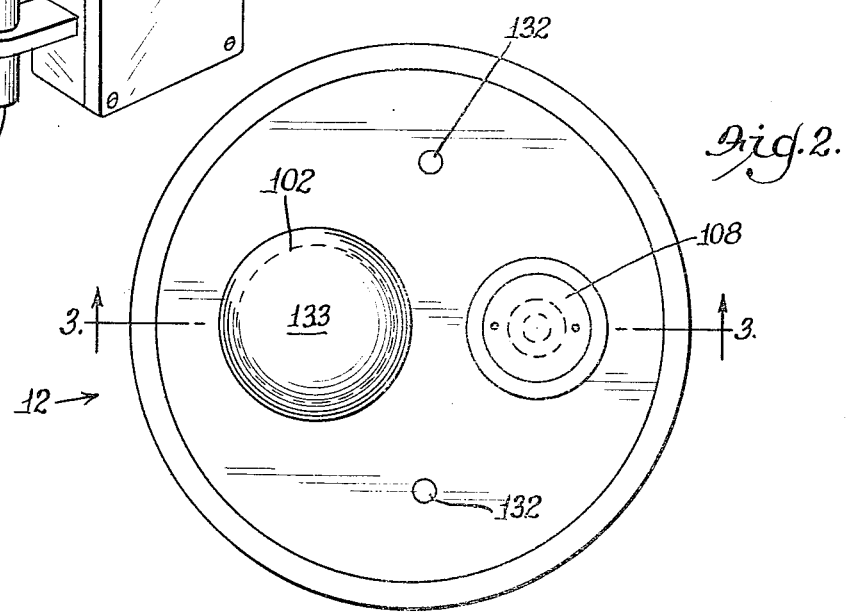
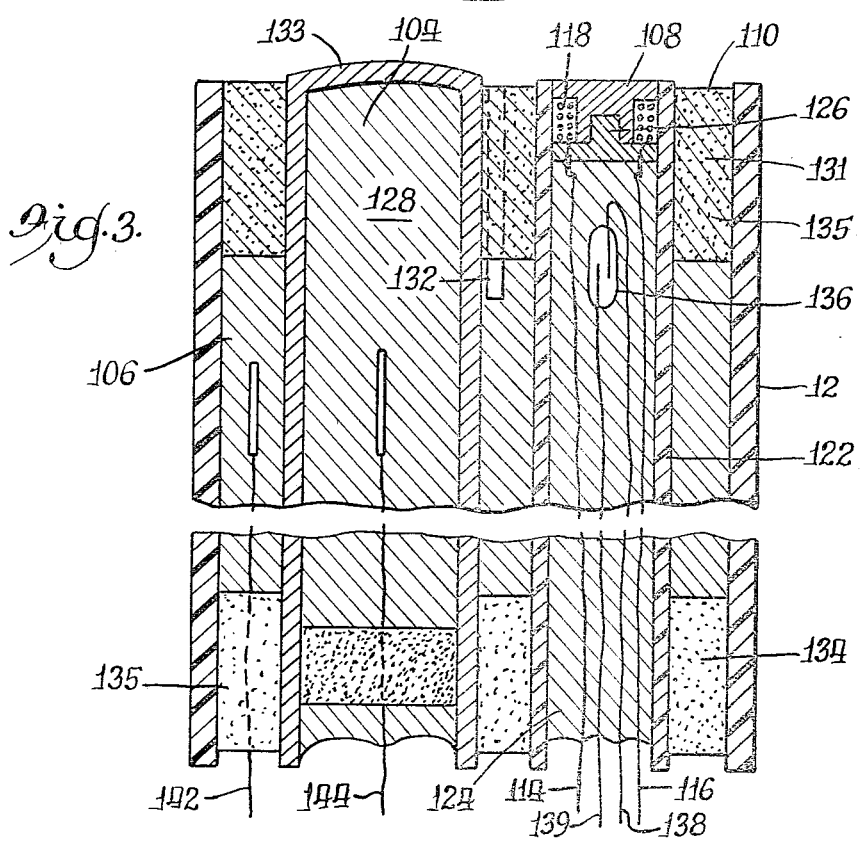

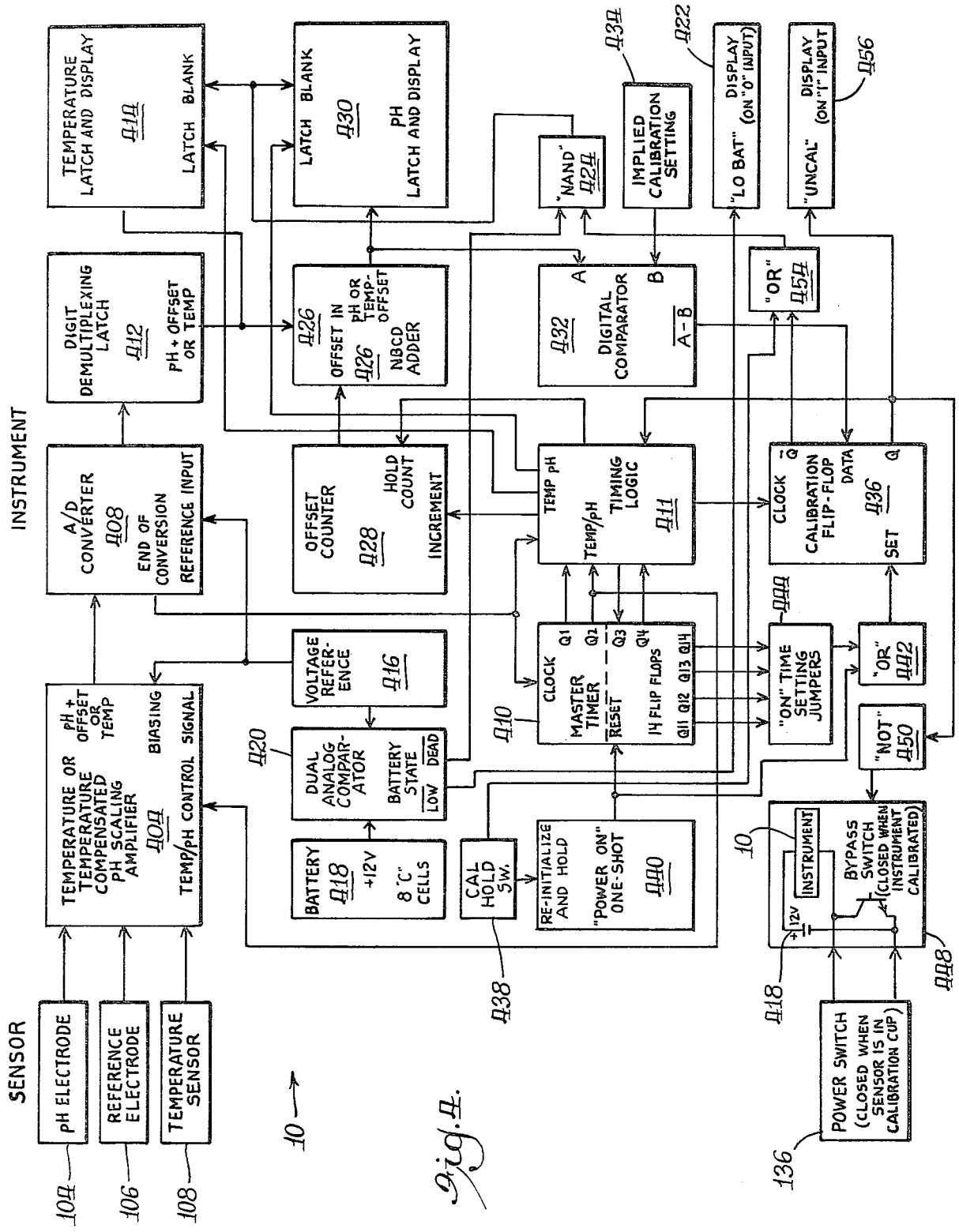

AUTOMATIC PORTABLE PH METER AND METHOD WITH CALIBRATION RECEPTACLE

The present invention is directed to methods and apparatus for pH measurement, and, more particularly, is directed to substantially fully automatic methods and apparatus for measurement of solution pH which may be particularly adapted for use by unskilled operators in a rugged operating environment such as that encountered in the measurement of pH of drilling fluid in oil well drilling environments or in field measurement of pH for water quality testing.

The measurement and determination of solution pH, or negative log of hydrogen ion concentration, is utilized on a routine basis in many industrial processes. For example, the pH of well drilling muds is routinely measured during drilling operations and the pH information thereby obtained may be utilized in mud formulation and property maintenance, as well as in monitoring or logging of geological formations being drilled. However, many mud engineers or technicians are not skilled in the proper calibration and care of pH instruments, and may not be capable of recognizing circumstances which result in inaccurate pH readings. Further, the rugged environment of a drilling rig where these measurements are made can be a further cause for inaccurate pH measurements or instrument malfunction. Accordingly, a portable pH meter that is capable of substantially reducing calibration and maintenance problems, and which is capable of providing for accurate and reliable pH measurements would be desirable.

Accordingly, it is an object of the present invention to provide improved methods and apparatus for the determination of pH. These and other objects of the invention will be more particularly set forth in the following detailed description and the accompanying drawings of which:

FIG. 1 is a perspective view of an embodiment of apparatus in accordance with the present invention;

FIG. 1B is a cross section through line 1—1;

FIG. 2 is a top view of the pH electrode assembly of the apparatus of FIG. 1;

FIG. 3 is a cross section side view of the electrode assembly of FIG. 2 taken through the line of 3—3;

FIG. 4 is a block circuit diagram of the apparatus of FIG. 1; and

Figure 5A:
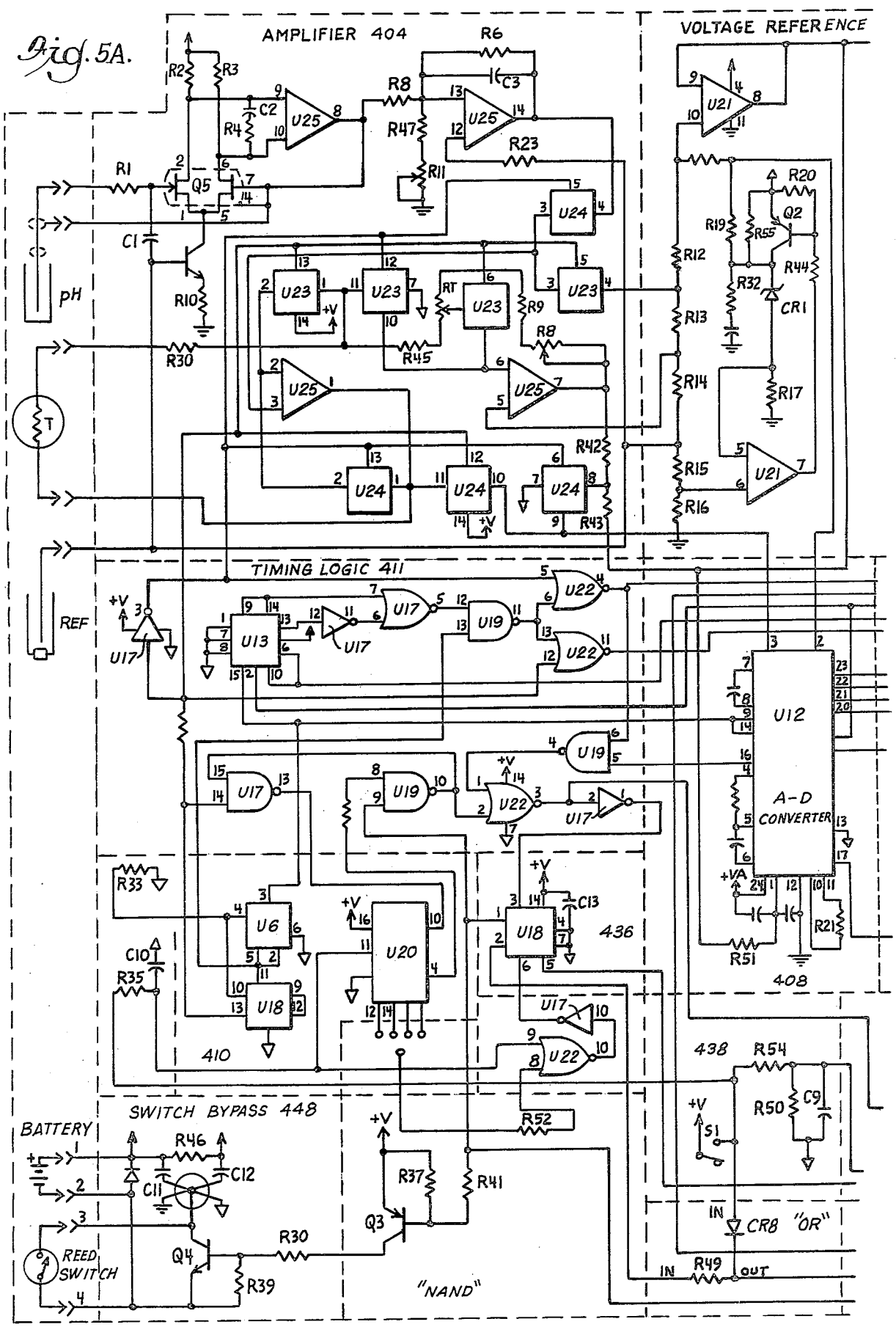
FIGS. 5a and 5b are a circuit diagram of the apparatus of FIG. 1, drawn such that the right hand side of FIG. 5a joins with the left hand side of FIG. 5b to form a continuous circuit diagram.

Generally, the present invention is directed to methods and apparatus for measurement of pH having a predetermined calibration and measurement cycle, which cycle is activated upon insertion of an electrode element into a calibration solution reservoir element which is interactive therewith. The instrument is provided with means for sensing the placement of the electrode element in the reservoir element, and adapted to respond to such placement of the electrode element in the reservoir containing a calibration solution of predetermined pH by automatically calibrating itself for subsequent use, for a predetermined period of time, in sample pH measurement.

The electrode element may comprise a pH electrode and a reference electrode for determining hydrogen ion electrochemical potential. The electrode element may further comprise a temperature sensor for purposes of temperature compensation of the hydrogen ion electrochemical potential. Because it is desirable to know the temperature of the solution for which a pH is being determined, and because temperature measurements must be made to provide temperature compensation to the $H^+$ electrochemical potential of the electrode, it follows that it is both convenient and easy to also provide means for displaying the temperature of the solution along with its pH.

The operational cycle of the system includes a calibration of the apparatus with a calibration solution of known pH. The apparatus may be calibrated by placement of the electrode element into a calibration solution reservoir element containing an appropriate buffer calibration solution. In this connection, it is an important feature of the present invention that means are provided for detecting the placement of the electrode element in a calibration reservoir element. Such means may desirably comprise a magnetic reed switch activatable by a magnetic field upon appropriate insertion of the electrode element into the calibration reservoir element. Such a system may utilize the electrode element and calibration reservoir as active and passive components, respectively, by physically integrating the magnetic reed switch in the electrode element, and by providing the reservoir component with one or more permanent magnets which provide a magnetic field sufficient to activate the switch upon appropriate insertion thereof into the reservoir. However, such means for detecting the location of the electrode element in the calibration reservoir may also comprise various circuit components other than a magnetic reed switch-magnet system. For example, the electrode element may incorporate a Hall-effect device which is adapted to detect the magnetic field at the interior of a calibration receptacle provided with appropriate magnet elements. Similarly, a mechanical switch such as a hemispherical depression switch (either on the electrode element or in a calibration receptacle) may be adapted to be activated by insertion of a cooperatively close-fitting electrode element—calibration receptacle combination. Moreover, a light emitting diode (LED) and photo detector (such as a photo detecting transistor) system may be used to detect the proper placement of the electrode element in a calibration receptacle. While one of the LED-photo detector components may be incorporated in the electrode and the other in a calibration receptacle, the calibration receptacle may be maintained, for example, as a passive device, if desired, by incorporating the LED and photo detector in the electrode element and by providing an appropriate reflector in the receptacle to reflect light from the LED to the photo detector when the electrode is appropriately positioned in the receptacle.

It is also possible to detect the location at the electrode with respect to the calibration reservoir by replacing the reed switch with circuit means for detecting the change in capacitance as the electrode is inserted into the solution in the calibration reservoir. This may be accomplished by mounting plates inside of the sensor body so the difference between the dielectric constant of the air and of the calibration solution as the probe is moved therebetween causes change in capacitance. This change in capacitance can be easily detected by measuring the phase shift or frequency change in an oscillator that uses this capacitance to control its frequency of oscillation. Similarly, an inductive detector circuit may be provided in a manner similar to such a capacitance detector circuit, if the reservoir is made of material that is magnetic, and the change in inductance is appropriately detected (e.g., by phase shift or oscillator frequency change).

In accordance with the present invention, upon detection of the placement of the electrode in the calibration receptacle, an automatic calibration procedure is begun, and in this connection, means are provided for calibrating the instrument desirably at measured temperature conditions in respect of a calibration solution of predetermined pH value. If the calibration procedure is successful, the instrument is placed in a sample measurement mode for a predetermined period of time during which analytical measurements such as measurement of drilling mud pH may be made, and then the instrument automatically turns itself off. Suitable timing means for clocking a predetermined measurement period and for turning off the instrument may be provided as will be further described. However, if the calibration procedure is unsuccessful, the instrument will not turn on thereby not giving the operator an opportunity to take an incorrect sample measurement. In this connection, it is an important feature of the invention, cooperatively with other features, that the instrument is adapted to test for a successful calibration. In this regard, problems such as operator error in the use of an improper or stale calibration solution, electrode or instrument failure or other operator error are tested for as a precondition for readying the instrument for sample measurement. If a successful calibration is not achieved, the instrument will not turn on so that potentially inaccurate pH sample measurements may not be made.

Having generally described various aspects of the invention, the invention will now be more particularly described with reference to the specific embodiments illustrated in the drawings. In this connection, illustrated in FIG. 1 is an embodiment of a portable pH meter in accordance with the present invention.

The apparatus 10 comprises a sensor electrode element 12, a control unit 14, a cable connection 16 between the element 12 and the control unit 14 and a calibration reservoir cup element 18 adapted to interact with the pH electrode element in a manner which will be explained in more detail hereinafter. In the illustrated embodiment, the calibration reservoir is formed as an integral part of a portion 11 of the handle assembly of the instrument 10 (also, including the electrode sensor 12), but the calibration reservoir element may also be a separate element apart from the other elements.

In this regard, the handle portion 11 of the instrument 10 is a polycarbonate plastic body having bored therein a cylindrical recess 13 with an inside diameter slightly larger than the outside diameter of the electrode sensor element 12 so as to permit insertion of the element 12 therein. When the instrument 10 is to be used, it may be placed on its back, so that the reservoir recess faces upward to receive and retain a pH calibration solution. The bottom of the recess forming the calibration reservoir cup element 18 may have a rim or other appropriate contour to protect the sensor components from physical contact with the bottom of the recess, as may be appropriate.

Also molded into the handle assembly portion 11 in symmetrically surrounding relationship to the cylindrical recess 13 are a plurality of permanent magnets 216, shown by dotted lines, which form a part of the means for detecting the placement of the electrode 12 in the reservoir element 18, as will be more fully described. The electrode element 12 itself is similarly of cylindrical shape adapted to form a handle upon insertion through cylindrical bore 15 of handle portion 17, and into a cylindrical bore (not specifically shown) in the handle portion 11 which also accommodates the recess 18. This configuration also protects the sensor element. Appropriate means, such as a spring loaded ball element cooperating with a suitable depression may be provided to retain the element 12 in those recesses as a handle until it is desired to remove the element 12 for calibration and measurement purposes. Means such as a moistened piece of cotton for keeping the sensor element moist may also be provided in the handle recess of the handle portion 11.

The electrode sensor circuit 12 is shown in more detail in FIGS. 2 and 3, and various of the sensor components of the electrode element 12 are shown in more detail in these figures. In this connection, the element 12 comprises a reference electrode element and pH electrode assembly 102 including a pH electrode 104 and a reference electrode 106. The electrode assembly 12 further includes a temperature probe element 108 at the distal, sensing end 110 of the electrode element 12, which is provided with electrical connection by means of wires 114, 116 for resistance sensing of the temperature at the end of the electrode element 12.

The wires 114, 116 are connected to a balco wire coil 118 or some other suitable material, which is in suitable thermal conductivity relationship with the solution to be measured such as by conductor plastic element 120. The temperature probe element is housed in a cylindrical plastic tube 122, and is mechanically integrated with a dielectric potting material 124. Electrical connection to the resistance elements 118 by wires 114, 116 is made through a plastic header 126 and the element is accordingly hermetically sealed from contact with the solution or drilling mud to be tested.

As shown in FIGS. 2 and 3, the reference electrode and pH electrode elements 104, 106 are filled with appropriate internal electrochemical filling solutions 128, 130. The reference electrode makes electrical contact with the sample solution by means of ceramic junctions 132 which penetrate a silicone seal 135 at the distal end of the electrode to the internal filling solution of the reference electrode. The pH electrode 104, as indicated in the drawing, makes direct contact with the sample through the pH glass end surface 133. Also provided in the electrode element 12 is a magnetically operated reed switch 136 which is disposed adjacent the distal end of the electrode element within the potting material of the cylinder 122. The reed switch is provided with electrically conducting wires 138, 139 and makes electrical contact between these wires when the reed switch is placed in a suitable magnetic environment, such as that provided by the magnets embedded around the reservoir recess 18 of the instrument 10.

At the proximate end 133 of the electrode assembly 12, the pH electrode element 104, and the conduit housing the temperature probe are similarly hermetically sealed by silicone and/or potting material 134, with the respective electrical contacts being formed in the cable 16 which connects to the control unit 14.

The reference electrode 106 and the pH electrode 104 provide an electrochemical potential signal to the controller 14 by means of conductors 142 and 144. The electrochemical potential signal thus provided is an uncompensated signal corresponding to the electrode potential of the electrochemical cell comprised of the reference and pH half-cells, and thus represents an uncompensated pH signal. Upon initiation of a calibration cycle, this uncompensated signal is subjected to calibration in the controller 14 to provide a compensated signal as will now be more fully described.

The instrument 10 is powered on and the calibration cycle begins by insertion of the electrode 12 into the illustrated calibration reservoir 18. In this connection, the pH electrode element 12 is cylindrical in exterior shape having a relatively flat distal end, and the pH electrode element 12 is adapted to be inserted into the calibration reservoir 18 when the instrument 10 is placed on its back. The calibration reservoir 18 is shaped to form a cylindrical bore as shown in FIG. 1. The bore may be adapted to receive a pH buffer solution of specific, predetermined pH value, which may be in the form of a one-use packet containing a pH calibrated buffer solution of desired pH value. The packet may be a disposable unit, the top seal 212 of which may be adapted to be broken by insertion of the pH electrode element 12 into the cylindrical bore 13 of the calibration reservoir 18. Further, the calibration reservoir 18 of the illustrated embodiment is provided with a plurality of (four) permanent magnetic elements 216 which are equilaterally spaced about the cylindrical bore 13 of the calibration receptacle. Upon insertion of the electrode element 12 into the bore 13 of the calibration receptacle 18 containing a fresh packet of calibration solution, the electrode will immerse the pH electrode sensing element 104, the reference sensing element 106, the electrical contact to the solution being made through ceramic junction 132, and the temperature sensing element 120 in the calibration solution. Further, upon insertion of the electrode element 120 into the calibration receptacle 18, the magnetic field of the magnets 216 will cause the magnetic reed switch 136 to close and make electrical contact between the wires 138 and 139 of cable 16. This provides a signal to the control unit 14 that such electrical contact in a calibration mode has been made, and initiates an operational cycle of the control unit 14, beginning with the calibration portion of the cycle.

The instrument is turned on and a calibration cycle is begun in the illustrated embodiment immediately upon activation of the reed relay 136 by insertion in the magnetic field of the calibration receptacle. There is no separate "off-on" switch on the control unit 14 which must be used by the operator. Initially, upon such activation of the instrument, digital displays 11A will not show any numbers, but the symbol "UNCAL" will appear on the LCD display to advise the operator that the instrument is presently uncalibrated. After an appropriate predetermined time interval, which for example, may be established to be about 90 seconds, the electrode probe 12 signal voltage will become temperature stable and will have reached its substantially final value. At this time, the internal electronics of the control circuit 14 will automatically temperature-compensate, and calibrate this signal to cause the digital readouts 11A to display simultaneously the pH value of the calibration buffer solution in the calibration receptacle, and the temperature of the buffer. However, the temperature compensated pH signal must be within a predetermined range of the nominal pH buffer value, or further use of the instrument will be prevented. The illustrated embodiment is adapted for calibration utilizing a buffer solution having a nominal pH value equal to 7.0, although it will be appreciated that other predetermined buffer pH values may also be utilized.

In the electrical circuitry of the illustrated control unit 14, it is assumed that in normal use only the electrode potential intercept (essentially the "zero adjust") will generally require regular compensation or adjustment, and that slope changes other than those which are caused by temperature variation will be substantially insignificant over the effective life of the electrode element 12. In this regard, tests on pH sensor slope change in drilling mud environments have shown only minor slope changes. However, it will be appreciated that means may be provided for compensating for such pH electrode slope changes if desired, such as by providing a calibration cycle requiring use of two different buffer solutions of different predetermined pH values. In any event, both "zero intercept" and temperature slope compensation are provided by the illustrated control unit 14. Temperature compensation of the electrode potential signal is carried out electronically based on temperature measurements made directly in the probe during immersion in the solution being measured.

As previously indicated, the electrical circuitry of the control unit 14 of the illustrated embodiment has only a predetermined degree of calibration latitude to calibrate for only a predetermined amount of drift or error in the system. The illustrated embodiment is adapted to compensate for ±0.5 pH units. Such errors may come from sthe calibration solution, probe drift or electronic drift. If the instrument has drifted so that the calibration capability of the instrument is inadequate, it is a feature of the embodiment 10 that the instrument will not display any pH or temperature values but will continue to display the symbol "UNCAL". In this connection in the illustrated embodiment, if the instrument has drifted more than +0.5 pH units, this is regarded to constitute an unsuccessful calibration cycle, and the instrument will perform as described above to prevent possibly erroneous data to be taken by the operator. If the instrument calibration range is sufficient to carry out the necessary calibration, the symbol "UNCAL" will disappear from the digital display unit 11A and the instrument will remain calibrated in the "on" condition for a predetermined length of time. In the illustrated embodiment, a nominal "on" time period of ten minutes is provided for taking of pH and temperature measurements before the instrument automatically turns off, although other "on" time periods may readily be provided.

The logic of the circuitry of the instrument 10 is adapted to prevent data errors from inadvertent (or even intentional) operator error or interruption of the intended measuring signal during the calibration cycle. In this connection, various potential causes of operator error have been accounted for in the operating cycle of the instrument 10. For example, if the electrode element 12 is placed in the wrong buffer (other than the designated calibrated buffer having a pH value of 7.0), there will be more than ±0.5 pH unit error to compensate for, and the instrument will turn off. Further, if the electrode probe 12 is pulled out of the calibration solution before calibration or during the calibration cycle, the instrument will turn off. If the batteries are too low for the control unit 14 to provide a correct reading for pH and temperature, the symbol "LOBAT" will appear on the display 11 to indicate this condition, and the instrument will not display numbers for pH or temperature.

Having generally described the embodiment 10, the electrical operation of the control unit 14 will now be more particularly described with reference to the circuit diagram of FIG. 4. Specific circuit elements of the device 10 are generally shown in FIG. 4, and are shown in detail in FIG. 5, to which reference may be made for a complete circuit specification. In connection with the block diagram of FIG. 4, the pH electrode 104, associated reference electrode 106, and temperature sensor 108 provide respective signals, as indicated in the figure which are directed to amplifier 404. Amplifier 404 is a scaling amplifier which is respectively adapted to amplify and output either the temperature sensor signal, or the pH-reference electrode signal, and provides an appropriate output signal to the analog to digital converter circuit 408. The selection of the operating mode of the amplifier 404, to output either the temperature signal or the pH signal to the A/D converter 408 is under the control of a temperature or pH control signal input to the amplifier 404 from the master timer circuit 410, as shown in FIG. 4. Initially in the calibration cycle, the master timer signal directs the amplifier 404 to select, amplify and output the pH signal to the A/D converter 408. The amplifier 404 scales the respective analog pH or temperature output signal so that digital conversion is in appropriate units for display (e.g., standard pH units, degrees celsius, etc.). Different amplifier circuitry for the respective analog pH and temperature information is used in the amplifier circuit 404 to accomplish the different scaling, or normalization requirements, as may be seen in FIG. 5, note 10.

As indicated, the amplified analog pH signal (or the analog temperature signal) is provided to the A/D converter 408, which is driven by an appropriate digital clock. The A/D converter 408 periodically converts the temperature or pH analog signal into a digital signal which is directed to the digital demultiplexing latch 412.

The temperature sensor 108 has an electrical resistance generally proportional to the temperature of the electrode element 12, including the pH electrode 104, reference electrode 106 and the temperature sensor 108, over the range of interest in solution testing. This temperature variable resistance may be utilized in a conventional manner for temperature-compensation of the pH signal by the amplifier 404 for temperature compensation of the pH reference electrode signal so that the analog pH signal supplied by the amplifier 404 to the A/D converter 408 and converted into digital form, is a suitably temperature compensated signal.

Appropriate voltage bias and reference input voltage for operation of the amplifier 404 and the A/D converter 408 is provided by voltage reference circuit 416 of the power supply system, which includes 12 volt battery 418, and dual analog comparator 420 which is adatped to indicate low or dead battery state respectively to low battery display 422, or the display blanking logic circuitry specifically including "NAND" circuit element 424 as shown in FIG. 4.

The temperature, or the temperature compensated pH output signal from the amplfier 404 is periodically and repeatedly converted to digital form by the A/D converter 408, which is driven by an appropriate clock. At the end of the periodic digital data conversion, the converter provides an end of conversion control signal which is directed to the master timer 410 and the timing logic circuit 411 to indicate completion of the digital conversion cycle. The digitally converted output from the A/D converter is provided to the digital demultiplexing latch circuit 412. Also, when in a temperature display mode under control of the temperature/pH control signal from the master timer circuit 410, this temperature information, following amplification by amplifier 404, as well as digital conversion by A/D converter 408 is directed from the digital demultiplexing latch 412 to the temperature latch and display circuit 414 for storage and display.

As indicated, the display of digital temperature and digital pH information from the A/D converter 408 to the digital demultiplexing latch 412 is under the control of the master timer 410 and the timing logic circuit 411.

Initially in the cycle, the digital output to the latch 412 represents uncalibrated digital pH data. This digital pH data from the digital demultiplexing latch 412 is directed to a natural binary coded decimal adder circuit. The other digital input to the NBCD adder circuit 426 is the digital output from the offset counter 428. The output from the NBCD adder circuit 426, which represents the sum of the digital inputs from the offset counter 428 and the digital demultiplexing latch 412, is directed to both the pH latch and display circuit 430 and the digital comparator circuit 432. The other input to the digital comparator circuit 432 is a digital implied calibration value from within the comparator circuit 432 corresponding to a preset pH value to be utilized by the device 10 and corresponding to a pH of 7.0 in device 10 illustrated in FIG. 4.

In addition to the digital pH signal input from the latch 412, the NBCD adder circuit 426 is also provided with digital information from offset counter 428, which increments under clock control until the digital comparator 432 determines equality between the implied calibration value in the comparator circuit 432, and the digital value of the signal provided by the NBCD adder circuit 426 to the digital comparator circuit 432. When the digital comparator 432 determines equality between the implied calibration value and the input from the NBCD adder 426, it provides appropriate equality indication signal to calibration flip-flop circuit element 436, which through timing logic circuit 411 directs a hold-count signal to the offset counter 428, to hold the equality inducing digital calibration correction value in the offset counter 428 for the subsequent utilization by the instrument 10. At this point, the flip-flop circuit element 436 also turns off "UNCAL" display 456 and, through "OR" gate 454 and "NAND" gate 424, turns on the pH and temperature display circuit elements 414 and 430, which are blank when "UNCAL" display 456 is on. The digital signal from the NBCD adder 426, which constitutes the summed numerical values of the uncalibrated digital pH signal from the A/D converter 408 and the calibration correction value from the offset counter 428, are displayed on the pH latch and display element 430. The numerical value of the offset counter is stored in the counter 428 as an offset (or "zero" intercept correcting) calibration value for subsequent addition to digital pH values from sample solution measurements during the particular run initiated by placement of the electrode 12 in the calibration receptacle 18. The NBCD adder is a natural binary coded decimal adder which utilizes 9's complement digital representation such that negative and positive numbers may be readily added together by the circuit.

Additional circuit elements of the instrument 10 comprise the magnetic reed power switch 136, which is closed ony when the electrode sensor 12 is placed in the calibration cup 18 in the instrument handle, and bypass switch 448 which closes only when the instrument 10 is successfully calibrated.

The battery power supply 418 and the remaining components of the instrument 10 are symbolically shown in the bypass switch block 448, because the magnetic reed power switch 136 and the bypass switch 448 control power supply to the entire instrument as there indicated. Thus, insertion of the sensor 12 into the calibration cup 18 closes the power switch 136 to provide power to the instrument to initiate a calibration cycle, and removal thereof from the cup 18 opens the switch. Similarly, the equality signal from the digital comparator 432, indicating a successful calibration, resets the calibration flip-flop 436, which logic status change is inverted by logic "not" element 450 and utilized to close the bypass switch 448. Prior to such closing of bypass switch 448, removal of the sensor 12 from the cup 18 will remove power from the instrument 10 and terminate the calibration cycle. The circuit further includes a calibration hold switch 438 which causes reinitialization of the instrument 10, and which provides appropriate signal to the power on one-shot circuit 440, which circuit is adapted, either upon initial power-up of the instrument 10 or upon activation of the calibration hold switch 438, to provide a signal input to reset master timer 410 and a signal input to logic "or" element 442 which resets the flip-flop circuit 436. In this way, the instrument is initialized for the calibration cycle. The illustrated calibration switch 438 when activated also signals logic "or" element 454, the output of which forms one input to logic "NAND" element 424, the output of which, in turn, turns on the pH and temperature display circuit elements 414, 430 even when "UNCAL" display 456 is on. The other input to logic "or" element 454 tests for the set condition of calibration flip-flop 436, which condition exists upon instrument power-up, prior to the completion of the calibration cycle, but which is changed by the equality signal from comparator 432 to flip-flop 436. Similarly the other input to NAND gate 424 is the dead batter signal output, which appropriately blanks the displays 414, 430. It should be noted that the calibration switch circuit 438 represents an optional operator control which may be eliminated from the instrument circuitry if no external controls are desired. The master timer 410, which is clocked by means of end of conversion pulses from the A/D converter 408, directs the timing logic circuit 411, provides the temperature or pH control signal to the amplifier 404, and controls the "on" time of the instrument through the "on time" setting circuit 444.

In operation of the device 10, insertion of the electrode sensor 12 into the calibration cup 18 of the instrument body closes the magnetic reed power switch 136, and thus initial application of power to the power-on oneshot circuit 440 resets the master timer 410, and sets the calibration flip-flop 436 through "or" gate 442. This, in turn, causes display of an "UNCAL" indication of the display by means of circuit 456, and blanking of the pH and temperature display circuits 414, 430. The initial resetting of the master timer 410 provides a low state temperature/pH control signal from output Q2 of timer 410 to amplifier 404, so that the A/D converter 408 receives pH signal information for every analog-to-digital conversion during the calibration cycle. The timer 410 waits a predetermined period of time (such as about 1 minute in the illustrated embodiment) to provide for establishment of thermal equilibrium. The timer 410 and the timer logic circuit 411 then engage the offset counter 428 by means of an increment enable signal directed to the offset counter as indicated in FIG. 4. The increment control signal from the timing logic circuit 411 causes the offset counter 428 to increment at each of the A/D conversions of the pH signal information from the amplifier 404 by the A/D converter 408. The periodically incrementing offset counter is combined in the adder 426 with the pH digital output signal from the digital demultiplexing latch 412. When the sum signal from the adder 426 is such that it equals the preset data numerical value from the calibration setting circuit 434 (pH 7.0 in the apparatus 10), the digital comparator circuit 432 signals an equality condition to reverse the logical status of the calibration flip-flop circuit 436. This calibration flip-flop status change is communicated to timing logic circuit 411, which in turn directs a "hold count" signal to the offset counter 428 in order to stop the incrementing of the counter and to hold the count achieved substantially at the time of the equality determination by the comparator 432. The timing logic circuit 411 also signals the calibration flip-flop change to the master timer 410, which begins commutation of the temperature/pH control signal to the amplifier 404 so that the amplifier alternately, with each "end of A/D conversion cycle" signal clocked into the timer 410 and logic circuit 411 from A/D converter 408, directs temperature or pH information into the A/D converter.

When the temperature/pH control signal is "high" the amplifier 404 and A/D converter 408 will output a signal representing the temperature of the sensor 108, which is normally between −99 and +99 degress celsius. When the temperature/pH control signal is "low", the amplifier 404 and the A/D converter 408 will output an uncorrected pH signal which is nominally between 0 and 19.9 pH units (although actual aqueous readings will not exceed pH 14). The timing logic circuit concomitantly controls display of temperature and pH information, respectively, at displays 414, 430, as shown in FIG. 4. This status change of the calibration flip-flop circuit 436 also closes the switch bypass circuit 448 via logic NOT gate 450 so that the user may then remove the electrode sensor 12 from the calibration cup 18 while maintaining power to the instrument. In this manner, the user may remove the electrode element 12 from the calibration cup 18 after temperature equilibration and calibration of the instrument and the power will stay on. However, if it is attempted to remove the electrode element 12 before such equilibrium is established and before calibration, the instrument will not stay on, because the switch bypass circuit 448 has not been activated and the maintenance of power to the instrument is dependent upon maintenance of the electrode element 12 in the calibration cup 18. The switch bypass circuit 448 will subsequently remain activated for a predetermined period of time under control of master timer 410 and on time setting jumper circuit 444 to permit the user to make measurements in drilling muds or some other solution to be measured.

After such a predetermined period of time (e.g., from about 5 to about 30 minutes) from the time the flip-flop is set by the digital comparator 432, the master timer 410 resets the flip-flop 436, opens the switch bypass 448, and accordingly turns the instrument off.

After a predetermined period of time (e.g., 15 minutes) from the time of setting the calibration flip-flop 436 (which time is determined by the "on" time setting jumper circuit 444), the calibration flip-flop circuit 436 is reset by logic "or" circuit 442, the switch bypass circuit 448 is opened and the instrument is automatically turned off to conserve the battery power of the instrument. It should also be noted that the digital comparator circuit tests during the calibration cycle to determine whether the calibration buffer solution is within a predetermined pH "window" or range of the calibration value of circuit 434, which may be, for example, ±0.5 pH units. If the calibration offset from counter 428 would exceed this value, the instrument 10 will not calibrate, the equality signal will not be generated by comparator 432, and the instrument will automatically turn off when the electrode is removed from the calibration cup.

The instrument may only be used again following successful completion of another calibration cycle, which in turn may be initiated when the reed relay embedded in the pH electrode probe is closed by the magnetic field of the calibration cup structure. In the illustrated embodiment, careful implementation of the prerequisite coordination of successful instrument calibration and instrument off-on function with instrument utilizability makes incorrect or improper use of the instrument in measurement function almost impossible. The instrument is automatically on and calibrated at the time the pH electrode is inserted into the calibration solution, and is also subsequently turned off automatically. According, no unexpected dead battery condition will result because an operator forgot to turn off the instrument. Further, it is substantially impossible to use the instrument if it cannot properly automatically calibrate itself or if the batteries are low. Further, by using prepackaged disposable pH buffer packets, vials or ampules, contamination error (such as through overuse or exposure of the buffer calibration solution) may be avoided. In this connection, in various different embodiments, the pH electrode element may be inserted into a calibration fixture (which may be separated from, or a part of the instrument body or handle) which is adapted to accept a small vial of glass, plastic or other effectively inert material filled with the buffer solution of desired, predetermined pH and which has a sealed top. The electrode probe 12 may be pushed through the top of the vial to break the seal, and accordingly, it may be made a necessary condition to the operation of the instrument to provide a small quantity of sealed calibration solution that must be discarded after each use. This feature may be used to substantially eliminate the use of stale or contaminated buffer solutions which could cause errors. It may thus be made substantially impossible for an operator to calibrate the instrument in the wrong buffer through operator error. On the other hand, fresh buffer solutions may be poured into a receptacle 18 such as shown in FIG. 1, from an individual vial or ampule (preferably) or a larger container of pH buffer solution for each calibration. The instrument further has automatic zero intercept and temperature compensation, so the digital pH reading which the instrument permits the operator to make on a particular sample may be regarded to be a substantially reliable and accurate value.

Figure 5B:
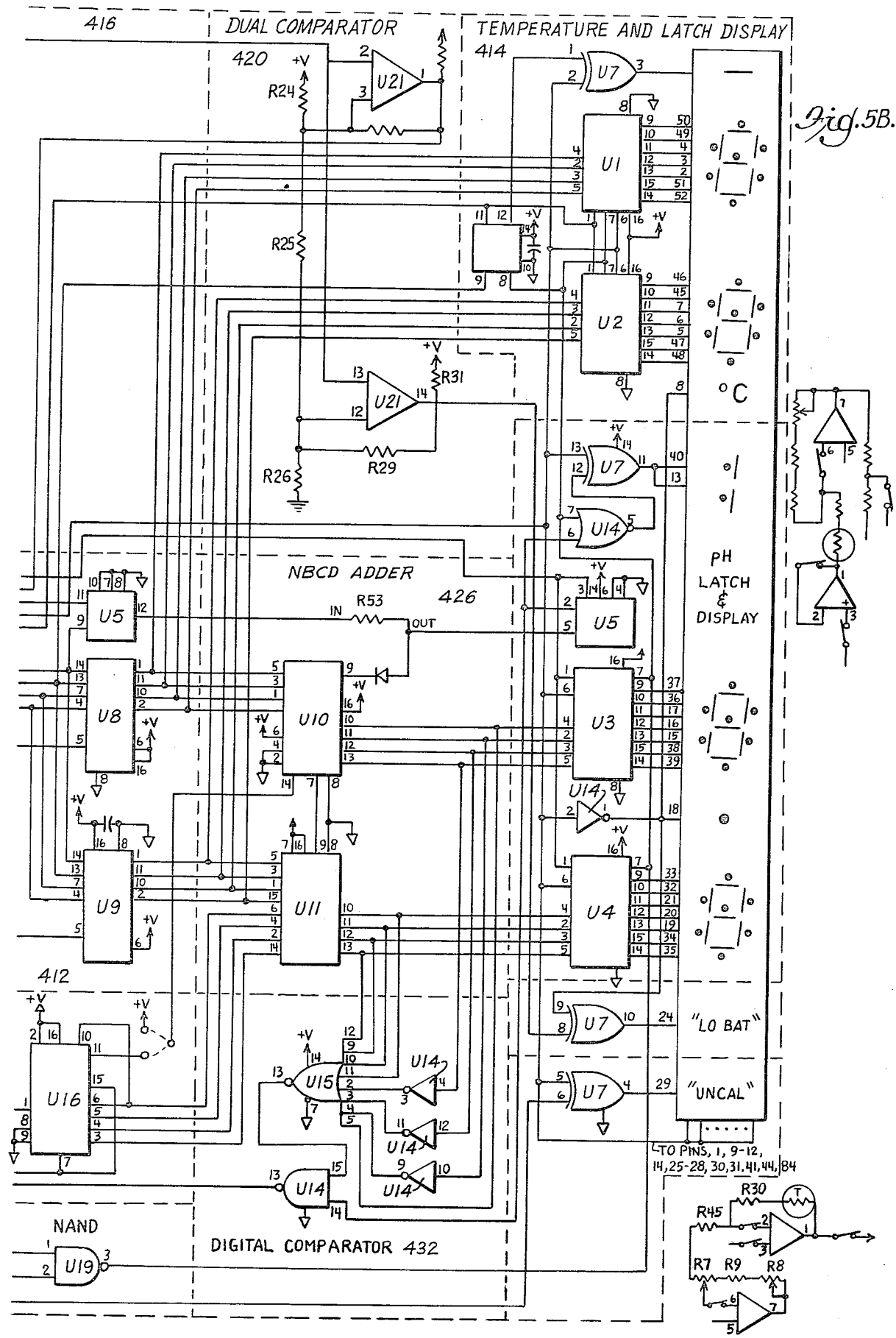

Specific details of the circuitry components of the instrument 10 are shown in the schematic component diagram of FIG. 5, in which various of the circuit elements of FIG. 4 are shown enclosed by dashed lines. In FIG. 5, resistor values are shown in ohms, and capacitor values in microfarads, unless otherwise noted. The unlabeled diode components are IN4148 diodes, unless otherwise noted. Various specific circuit components are identified in Appendix A attached hereto.

The illustrated circuit may readily adjust various operating parameters by component changes. For example, the calibration window, or acceptable range of match of calibration buffer solution measurement with the preset calibration setting may be varied by internal pin switch position W2 and resistor selection as follows:

|  | Calibration Window | |
| --- | --- | --- |
|  | 2 pH Units | 1 pH Unit |
| R9 | 750 | 825 |
| R13 | 249 | 200 |
| R45 | 255 | 200 |
| W2 | POS. 2 | POS. 1 |

Similarly, the "on time" of the instrument may be varied by internal pin switch position selection of element W1 of the on-time circuit, as follows:

| "On" Time After Cal in Min. | W1 POS |
| --- | --- |
| 3 | 4 |
| 7 | 8 |
| 15 | 16 |
| 31 | 32 |

The illustrated system utilizes digital liquid crystal display, which prevents misreadings by an unskilled operator such as might be obtained with analog metal needle displays. In the simplest embodiments, there are not adjustments or controls that are accessible to the operator from outside the case, and there is correspondingly reduced opportunity for operator error or misuse of the instrument. The case 13 of the control instrument 10 may be readily made water tight and submersible in liquids because there are no access holes required for external adjustment.

The control unit 14 of the illustrated embodiment has a completely sealed case, which is waterproof, and mechanically rugged. The control unit has no external adjustments or knobs or switches, and in fact, is not even provided with an "off-on" switch other than the switch means for indicating placement of the electrode sensor element 12 in the calibration cup. As indicated, the apparatus 10 has automatic temperature compensation, fail safe automatic "zero adjust" calibration, and a digital display showing pH temperature and instrument function operation. The instrument may be provided with long instrument battery and sensor life (e.g., 1 year battery life, 1 year sensor life, and low sodium error). The instrument is sufficiently rugged and is provided with a molded polycarbonate plastic box with waterproof gaskets to make it possible for the entire unit control box 14 to be completely submerged in water or mud and yet be washed with a hose and still work without damage. It will thus be appreciated that the illustrated instrument 10 is a reliable and effective portable system for obtaining accurate pH measurements in adverse environments.

The instrument has rugged construction features desirable for adverse environments. In this connection, the pH probe element similarly contains pH, reference and temperature compensation elements all unified in a single, rugged, plastic body. The tip of the probe has no bulb, but rather employs a flat pH glass configuration that is easier to protect from breakage and is easier to clean. The electode probe is stored in such a way that it becomes the instrument handle which is particularly adapted to protect the electrode and keep it moist.

In this connection, the distal end of the electrode probe is adapted to be inserted in a cylindrical recess in the upper handle element of the instrument, and the sensing element may be effectively hermetically sealed therein by means of an internal eastomeric material in the recess which engages the cylindrical sides of the electrode probe. Suitable means for maintaining the atmosphere in moist condition, such as moistened cotton, or synthetic sponge material may also be placed at the interior of the storage recess to provide for desirable storage condition for the electrode elements.

Another desirable feature of this arrangement is that by properly inserting the sensing element into the appropriate recess it becomes a convenient handle for carrying the instrument. The sensing element will last longer and have a faster response time if it is kept moist just prior to use. This feature helps cause an unskilled user to keep the sensing element wet because it is more convenient having a handle when the instrument is to be transported.

The upper handle element also has a calibration recess for use with the instrument in a horizontal position. The calibration reservoir thereby provided comprises means for signalling the proper positioning of the electrode probe in the reservoir, which in the embodiment comprises a plurality of permanent magnets capable of activating the reed relay in the electrode probe. However, it should be appreciated that the physical integration of the calibration reservoir with the control unit provides for additional active testing or instrumentation in the reservoir.

The principal electronic components are housed in a rugged waterproof box, which may be made, for example, of a tough, durable plastic material. Calibration and operation are fully automatic, so the instrument need have no adjustment knobs. The digital readout is a liquid crystal display which displays pH to one decimal point, temperature in ° C. and the words "UNCAL" or "LOBAT" when these conditions occur.

In use by an operator, in simple operational terms, a small sealed 2 ml vial of prepackaged buffer solution (sufficient for one calibration) may be opened and poured into the calibration cup which is built into the instrument handle. The electrode probe may be removed from its storage position in the instrument handle and inserted in the calibration cup. The instrument display will read "UNCAL". In approximately 60 seconds, the instrument automatically calibrates itself, "UNCAL" goes out and pH=7.0 appears along with the temperature of the calibration solution. If the electrode, the electronic circuits or the buffer are out of a predetermined calibration range, the instrument won't display pH or temperature but will continue to read "UNCAL" until the probe is removed from the calibration cup. The instrument will then turn itself off.

Once the pH=7.0 reading appears, the instrument can now be used by the operator to make fully temperature compensated pH measurements for approximately the next 15 minutes. At the end of this time, it shuts itself off. To be used again, the calibration cycle must be repeated, in order to insure accurate measurements. If the electrode probe is removed from the calibration solution before the 60 second stabilization interval is complete, the instrument will turn itself off. If the electrode is momentarily removed during the 30 second stabilization interval and then reinserted, a full 30 seconds from the time of reinsertion will be required before calibration can occur.

The instrument uses eight standard "C" alkaline batteries and has a battery life of 400 hours. When there are about 8 hours of use left, the display will read "LOBAT" but the instrument will continue to operate normally. When the batteries are so low they could give unreliable readings, the pH and temperature displays go out and only the symbol "LOBAT" remains.

Accordingly, it will be appreciated that through the present invention, portable pH measuring systems have been provided which are effective for reliable pH measurement under non-laboratory conditions by relatively unskilled operators.

However, while the present invention has been particularly described with respect to specific embodiments, it will be appreciated that various alterations, modifications, and adaptations will be apparent based upon the present disclosure and are intended to be within the scope of the present invention.

Various of the features of the invention are set forth in the following claims.

APPENDIX A

| Reference Designation | Description |
|---|---|
| U1-4 | Integrated Circuit MC14543BCP |
| U5-6,18 | Integrated Circuit MC14013BCP |
| U7 | Integrated Circuit MC14507AL |
| U8,9 | Integrated Circuit MC14042BCP |
| U10,11 | Integrated Circuit MC14560BCP |
| U12 | Integrated Circuit MC14433BCP |
| U14,17 | Integrated Circuit MC14572BCP |
| U15 | Integrated Circuit MC14078BCP |
| U16 | Integrated Circuit MC14518BCP |
| U19 | Integrated Circuit MC14011BCP |
| U20 | Integrated Circuit MC14040BCP |
| U21, 25 | Integrated Circuit LM324N |
| U22 | Integrated Circuit MC14001BCP |
| U23, 24 | Integrated Circuit MC14016BCP |
| U13 | Integrated Circuit MC14520BCP |
| DS1 | LCD Display |
| Q1 | Transistor 2N2484 |
| Q2,3 | Transistor 2N5087 |
| Q4 | Transistor 2N4401 |
| Q5 | Dual FET U425 |
| CR6 | Diode 1N4148 |
| C1 | Capacitor 100 pf Corning Glass 100V |
| C2,5,6,8,9, 11, 12, 13, 14, 15 | Capacitor 0.1 µf Ceramic 50 V |
| C3 | Capacitor 1.0 µf |
| C7 | Capacitor 0.1 µf Mylar 200V |
| C10 | Capacitor .01 µf Ceramic |
| C4 | Capacitor 15 µf 20V TANT |
| CR7 | Diode 1N4148 |
| CR1 | Diode Zener 1N4571 |
| CR5,8 | Diode Zener 1N4148 |
| CR3 | Diode Zener 1N4002 |
| CR2,4 | Diode Zener 1N4148 |
| (RS1,2) | Bifurcated Terminal |
| RS1,2 | Reed Switch MINI-25-115 |
| R32,46 | Resistor 10 ohms ¼W, 5% |
| R54 | Resistor 560 ohms ¼W, 5% |
| R51 | Resistor 1K ¼W, 5% |
| R20 | Resistor 2.2K ¼W, 5% |
| R4,28,31,44 | Resistor 4.7K ¼W, 5% |
| R48,50 | Resistor 10K ¼W, 5% |
| R33,34 | Resistor 10K ¼W, 5% |
| R10 | Resistor 15K ¼W, 5% |
| R36, 52 | Resistor 22K ¼W, 5% |
| R38,39 | Resistor 47K ¼W, 5% |
| R1,35,49,53 | Resistor 100K ¼W, 5% |
| R21 | Resistor 300K ¼W, 5% |

APPENDIX A-continued

| Reference Designation | Description |
| --- | --- |
| R41 | Resistor 560K ¼W, 5% |
| R40 | Resistor 560K ¼W, 5% |
| R37 | Resistor 1M ¼W, 5% |
| R27 | Resistor 10M ¼W, 5% |
| R55 | Resistor 22K ¼W, 5% |
| R19 | Resistor FACT. SEL. 1% RN55C |
| R30 | Resistor 165 ohms 1% RN55C |
| R13,45 | Resistor 200 ohms 1% RN55C |
| R13 | Resistor 249 ohms 1% RN55C |
| R45 | Resistor 255 ohms 1% RN55C |
| R18 | Resistor 402 ohms 1% RN55C |
| R16,17 | Resistor 499 ohms 1% RN55C |
| R12 | Resistor 549 ohms 1% RN55C |
| R9 | Resistor 750 ohms 1% RN55C |
| R9 | Resistor 825 ohms 1% RN55C |
| R15,25 | Resistor 1.00K 1% RN55C |
| R14 | Resistor 1.50K 1% RN55C |
| R23 | Resistor 16.5K 1% RN55C |
| R43 | Resistor 24.9K 1% RN55C |
| R26 | Resistor 34.8K 1% RN55C |
| R24 | Resistor 42.2K 1% RN55C |
| R47 | Resistor 47.5K 1% RN55C |
| R5,6 | Resistor 49.9K 1% RN55C |
| R2,3,22 | Resistor 69.8K 1% RN55C |
| R42 | Resistor 100K 1% RN55C |
| R7 | Resistor Var. 50 ohms |
| R8 | Resistor Var. 200 ohms |
| R11 | Resistor Var. 5K |
| R33,36,52, CR7 | Resistor 0 ohms (Jumper) |
| W1,POS 4 | Jumper X1 (3 Minute on Time) |
| W1,POS 8 | Jumper X2 (7 Minute on Time) |
| W1,POS 16 | Jumper X3 (15 Minute on Time) |
| W1,POS 32 | Jumper X4 (31 Minute on Time) |
| W2,POS 1 | Jumper |
| W2,POS 2 | Jumper |

What is claimed is:

1. A portable pH meter comprising,
an electrode probe comprising a pH electrode and a reference electrode for measuring hydrogen ion electrochemical potential of a liquid,
means for measuring the temperature at the reference and pH electrodes,
a calibration receptacle adapted to receive the electrode probe, and for containing pH buffer calibration solution of predetermined pH,
probe detecting means for determining the positioning of said electrode probe in said calibration receptacle,
calibration means activated by said probe detecting means, for calibrating the electrochemical potential measured by said probe while positioned in said calibration receptacle to a predetermined pH value corresponding to said predetermined calibration buffer pH, and
temperature compensation means for compensating the electrochemical potential measured by said probe in respect of the temperature measured by said temperature measurement means.

2. A portable pH meter in accordance with claim 1 wherein said calibration means comprises means for inactivating said meter if the calibration adjustment exceeds a predetermined value.

3. A portable pH meter in accordance with claim 1 further including means for maintaining power to said meter for sample measurement for only a predetermined limited period of time following calibration by said calibration means.

4. A portable pH meter in accordance with claim 1 further including means for activating said calibration means after a predetermined delay period following detection of the positioning of said electrode probe in said calibration receptacle by said probe detecting means.

5. A portable pH meter in accordance with claim 1, wherein said probe detecting means comprises a magnetic reed switch in said electrode probe and at least one permanent magnet positioned in or about said calibration receptacle.

6. A portable pH meter in accordance with claim 1 wherein said calibration receptacle is formed in a portion of an instrument body of said meter, and wherein the electrode probe is adapted to serve as an instrument handle when not utilized for measurement.

7. A portable pH meter in accordance with claim 1 wherein said meter further includes recess means for insertion of the electrode probe when not used for measurement purpose, and for maintaining a humid environment for said probe during insertion therein.

8. A portable pH meter in accordance with claim 1 wherein said meter uses a battery power source and further includes means for displaying the calibrated, temperature compensated electrochemical potential measured by said probe and for determining and indicating a predetermined low level of remaining battery life.

* * * * *